United States Patent
Kolberg et al.

(10) Patent No.: US 7,182,768 B2
(45) Date of Patent: Feb. 27, 2007

(54) CATHETER FOR CARDIOVASCULAR APPLICATION

(75) Inventors: Gernot Kolberg, Berlin (DE); Curt Kranz, Berlin (DE); Erhard Flach, Berlin (DE)

(73) Assignee: Biotronik GmbH & Co. KG, Berlin (DE)

( * ) Notice: Subject to any disclaimer, the term of this patent is extended or adjusted under 35 U.S.C. 154(b) by 631 days.

(21) Appl. No.: 10/419,264

(22) Filed: Apr. 21, 2003

(65) Prior Publication Data

US 2003/0229277 A1  Dec. 11, 2003

(30) Foreign Application Priority Data

Apr. 19, 2002  (DE) ............... 102 17 509

(51) Int. Cl.
  *A61D 1/12*  (2006.01)
(52) U.S. Cl. ............... 606/108; 607/119; 604/264
(58) Field of Classification Search ............ 607/115, 607/116, 119, 122, 123, 126, 128; 600/372–375, 600/381, 585; 604/164.01, 164.09, 164.13, 604/264, 523–527; 606/108; 128/899
See application file for complete search history.

(56) References Cited

U.S. PATENT DOCUMENTS

| | | | |
|---|---|---|---|
| 4,813,934 A * | 3/1989 | Engelson et al. ....... 604/99.02 |
| 5,167,637 A | 12/1992 | Okada | |
| 5,228,452 A | 7/1993 | Samson | |
| 5,348,537 A * | 9/1994 | Wiesner et al. ......... 604/99.04 |
| 5,356,381 A | 10/1994 | Ensminger | |
| 5,376,084 A | 12/1994 | Bacich et al. | |
| 5,380,307 A * | 1/1995 | Chee et al. ............. 604/264 |
| 5,752,938 A | 5/1998 | Flatland | |
| 5,928,203 A * | 7/1999 | Davey et al. ............. 604/247 |
| 6,017,323 A * | 1/2000 | Chee ..................... 604/96.01 |
| 6,024,729 A | 2/2000 | Dehdashtian | |
| 6,231,543 B1 * | 5/2001 | Hegde et al. ............ 604/96.01 |
| 6,306,124 B1 * | 10/2001 | Jones et al. .............. 604/509 |
| 6,432,091 B1 * | 8/2002 | Davey .................... 604/246 |
| 6,512,957 B1 | 1/2003 | Witte | |

FOREIGN PATENT DOCUMENTS

| | | |
|---|---|---|
| DE | 31 00 622 A1 | 2/1982 |
| DE | 196 39 870 C1 | 12/1997 |
| DE | 199 15 342 C1 | 10/2000 |
| DE | 199 30 266 A1 | 12/2000 |
| DE | 693 29 771 T2 | 8/2001 |
| EP | 0 468 645 A1 | 1/1992 |
| GB | 2 067 075 A | 7/1981 |

* cited by examiner

*Primary Examiner*—Cris L. Rodriguez
(74) *Attorney, Agent, or Firm*—Browdy and Neimark, PLLC

(57) ABSTRACT

A catheter for cardiovascular application includes
  an elongated catheter shank;
  a lumen inside the catheter shank;
  a mandrel sleeve that extends in the lumen;
  a guide wire which runs in the mandrel sleeve and is extendable through a sluice gate out of the catheter at a distal end thereof; and
  a sealing unit for sealing the lumen, the sealing unit being disposed proximally in front of the sluice gate and reversibly pierced by the replaceable mandrel sleeve.

7 Claims, 1 Drawing Sheet

CATHETER FOR CARDIOVASCULAR APPLICATION

BACKGROUND OF THE INVENTION

1. Field of the Invention

The invention relates to a catheter for cardiovascular application, comprising an elongated catheter shank; a lumen inside the catheter shank; a mandrel sleeve which extends in the lumen; and a guide wire which runs in the mandrel sleeve and is extendable through a sluice gate out of the catheter at a distal end thereof.

2. Background Art

Catheters for cardiovascular application also include for example electrodes for cardiac pacemakers or defibrillators which come in the most varying designs. Special problems are posed when these electrodes are to be positioned not only in the easily accessible atria or ventricles of the heart, but in hardly accessible cardiac vessels such as the coronary sinus.

U.S. Pat. No. 6,512,957 B1 teaches a catheter which is suitable for introduction into the coronary sinus or other hardly accessible blood vessels, in particular upon use as a cardiac pacemaker electrode probe. This catheter has an elongated catheter shank with a lumen which a sleeve-type mandrel—a springy, comparatively dimensionally stable guide sleeve—passes through. This mandrel houses a guide wire which can be led through a sluice gate out of the catheter at the distal end thereof.

This guide wire is pre-bent and used as a probe which may be advanced beyond the tip of the catheter in a direction that deviates from the straight direction of the catheter, owing to the pre-bent orientation of the wire. In this way it is possible to advance the pre-bent wire into a branch of the blood vessels, and then to follow up with the catheter that is guided by the pre-bent wire.

In spite of increased flexibility and, consequently, more precise guidance, this catheter needs improvement in several aspects. For example, the catheter is only intended to be led into the heart by a mandrel sleeve and guide wire, with the guide wire being used only in critical situations by extension and guidance for instance into a cardiac vessel. When the guide wire is led in separately from outside and the catheter is subsequently pushed along the entire length of the wire according to the so-called over-the-wire technique, there is the problem that the guide wire is subject to high friction by the sluice seal at the distal wire gate, which impedes in the catheter being pushed over the guide wire.

On the other hand, the mentioned catheter is intended for use only together with a guide wire, other designs being chosen for catheters for use with a mandrel. In this regard, prior art catheters are available which are conceived either for use together with a guide wire or with a mandrel. This will double manufacturing and stockkeeping requirements for catheters of otherwise identical design. These additional requirements also affect hospital logistics and stockkeeping.

SUMMARY OF THE INVENTION

Proceeding from the described prior art problems, it is an object of the invention to develop a catheter of the type mentioned at the outset for more universal use together with a guide wire or mandrel on the one hand and for smooth over-the-wire technique when used together with a guide wire on the other hand.

This object is attained in a catheter comprising a sealing unit, which is disposed proximally in front of the sluice gate, and is provided for sealing the lumen, the sealing unit being reversibly pierced by a replaceable mandrel sleeve.

Due to the fact that the mandrel is replaceable, the catheter according to the invention, for use without guide wire, may be equipped with a corresponding mandrel. If however the catheter is intended to be employed together with a guide wire, a mandrel sleeve is used which has a lumen for the guide wire and which, as against the prior art mentioned at the outset, pierces the sealing unit. By the aid of the mandrel sleeve cooperating with the sealing unit as a sealing partner, the lumen of the catheter is blocked against any blood penetrating. Simultaneously the guide wire can be moved unimpeded inside the lumen of the mandrel sleeve.

Attention is drawn to the fact that a hose or any other tubular object may be used as a mandrel sleeve according to the invention.

Preferably, a stop for the piercing motion of the mandrel sleeve is provided between the sealing unit and the sluice gate. This stop prevents the mandrel sleeve from being inadvertently pushed out of the catheter, affecting myocardial or vessel wall tissue. On the other hand, this stop works as an abutment for the mandrel sleeve which may conventionally serve for straightening the catheter shank in the vicinity of a pre-formed deflection of the shank.

In keeping with another preferred embodiment, a second stop is disposed proximally in front of the sealing unit, cooperating with a counterpart on a mandrel that is insertable into the lumen. This stop again serves as an abutment for the mandrel, on the other hand it prevents the mandrel from piercing the sealing unit upon operation without guide wire. This ensures reliable sealing of the catheter lumen even in this case of application.

Preferred embodiments of the invention relate to the stops being designed as graduations in diameter in the form of annular shoulders and the proximal stop cooperating with a ball on the counterpart of the mandrel without guide wire.

Preferably, provision is made for the mandrel, or mandrel sleeve and guide wire, to be insulated towards the electric connecting lines for the catheter electrodes, which helps obtain a potential-free guide wire. This helps avoid malfunctions of the catheter electrodes resulting from electric connection to the guide wire that rests in the blood stream.

Further features, details and advantages of the invention will become apparent from the ensuing description of an exemplary embodiment of the invention, taken in conjunction with the drawings.

DESCRIPTION OF THE PREFERRED EMBODIMENT

Figure 1:
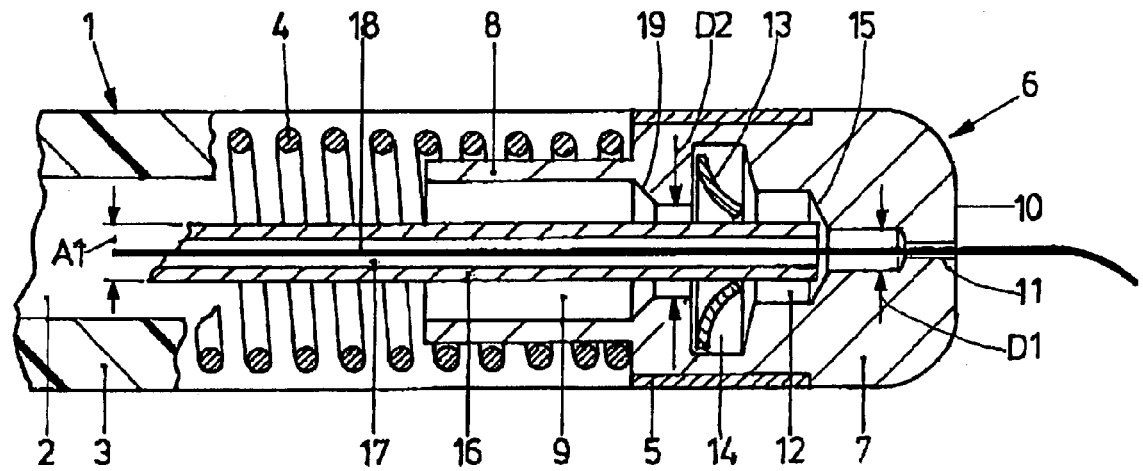
FIG. 1 is a view of an axial section through the distal end of a catheter with a guide wire inserted.
Figure 2:
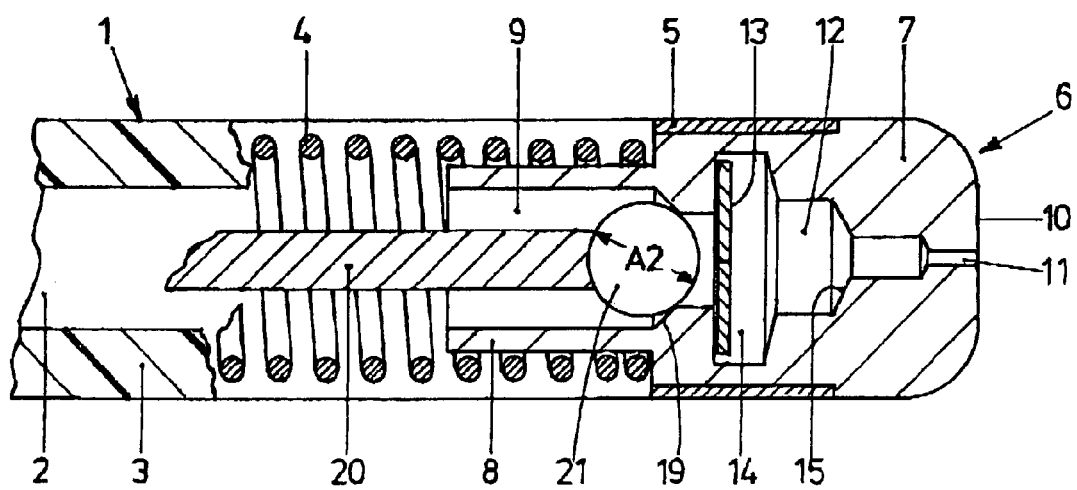
FIG. 2 is a partial sectional view, by analogy to FIG. 1, with a mandrel without guide wire inserted.

The catheter, details of the distal end of which are seen in FIGS. 1 and 2, comprises a catheter shank 1 that contains an axially continuous, central lumen 2. Provided within the wall 3 of the catheter shank is a spiral connecting line 4 for a ring electrode 5 which is disposed in an insulating head 7 that constitutes the distal end 6 of the catheter.

In the proximal direction, the head 7 includes an attached ring 8, with the distal end of the spiral connecting line 4 resting thereon, and with the central lumen 2 continuing through the interior aperture 9 thereof.

The distal front end 10 of the head 7 centrally comprises a sluice gate 11 which is accessible from the lumen 2 and the interior aperture 9 via a central passageway 12 within the head 7. Disposed proximally before the sluice gate 11 in this passageway 12 is a sealing unit 13 in the form of a flexible disk with a central expandable opening that is located in an annular chamber 14 of the passageway 12. Provided in the passageway 12 between the sealing unit 13 and the sluice gate 11 is a first distal stop 15 which results from a corresponding graduation is diameter. This is where the passageway 12, in continuation of the lumen 2, decreases to an inside diameter D1 which is less than the outside diameter A1 of a mandrel sleeve 16, the mandrel sleeve 16 extending within the lumen 2, piercing the sealing unit 13 and being blocked against further extension out of the lumen 2 by the dimensioning, mentioned above, in the vicinity of the distal stop 15.

Inside the central sleeve passage 17, a guide wire 18 is displaceable quasi freely and without any relevant friction relative to the mandrel sleeve 16 and to the catheter shank 1. Once the guide wire 18 has been led into the desired cardiac vessel, the catheter can be moved over the wire 18 without any problems. The lumen 2 is properly sealed by the sealing unit 13 towards any blood that might enter.

As further seen in FIGS. 1 and 2, a second, proximal stop 19 is provided in the form of a graduation in diameter at the bottom of the attached ring 8, with the inside diameter D2 thereof being distinctly greater than the inside diameter D1 of the first, distal stop 15. In particular, this inside diameter D2 exceeds the outside diameter A1 of the mandrel sleeve 16 so that the stop 19 will not impede the mandrel sleeve 16 in being pushed through the sealing unit 13 as far as to the distal stop 15.

If a conventional mandrel without a guide wire 18 is employed, the mandrel sleeve 16 can be removed and a mandrel 20 (seen in FIG. 2) can be inserted, bearing by a counterpart ball head 21 on its distal end against the stop 19. The outside diameter A2 of the ball head 21 is greater than the inside diameter D2 of the proximal stop 19. This prevents the mandrel 20 from being pushed through the sealing unit 13. The lumen 2 is kept properly sealed.

Embedding the connecting line 4 in the wall 3 of the catheter shank 2 provides for electrical insulation of the mandrel 20, or the mandrel sleeve 16 and the guide wire 18, towards the connecting line 4.

What is claimed is:

1. A catheter for cardiovascular application, comprising
an elongated catheter shank (1);
a lumen (2) inside the catheter shank (1);
a removable mandrel sleeve (16) which extends in the lumen (2);
a guide wire (18) which runs in the mandrel sleeve (16) and is extendable through a sluice gate (11) out of the catheter at a distal end (6) thereof; and
a sealing unit (13) for sealing the lumen (2), the sealing unit (13) being disposed proximal of the sluice gate (11) and reversibly pierced by the removeable mandrel sleeve (16).

2. A catheter according to claim 1, comprising catheter electrodes (5), wherein the mandrel sleeve (16) and the guide wire (18) are electrically insulated towards electric connecting lines (4) for the catheter electrodes (5).

3. A catheter for cardiovascular application, comprising
an elongated catheter shank (1);
a lumen (2) inside the catheter shank (1);
a removable mandrel sleeve (16) which extends in the lumen (2);
a guide wire (18) which runs in the mandrel sleeve (16) and is extendable through a sluice gate (11) out of the catheter at a distal end (6) thereof,
a sealing unit (13) for sealing the lumen (2), the sealing unit (13) being disposed proximal of the sluice gate (11) and reversibly pierced by the removeable mandrel sleeve (16), and
a distal stop (15) for the piercing motion of the mandrel sleeve (16) being disposed in the lumen (2) between the sealing unit (13) and the sluice gate (11).

4. A catheter for cardiovascular application, comprising
an elongated catheter shank (1);
a lumen (2) inside the catheter shank (1);
a removable mandrel sleeve (16) which extends in the lumen (2);
a guide wire (18) which runs in the mandrel sleeve (16) and is extendable through a sluice gate (11) out of the catheter at a distal end (6) thereof; and
a sealing unit (13) for sealing the lumen (2), the sealing unit (13) being disposed proximal of the sluice gate (11) and reversibly pierced by the removeable mandrel sleeve (16)
a proximal stop (19) being disposed proximal of the sealing unit (13) in the lumen (2), the second stop (19) cooperating with a counterpart (21) on a mandrel (20) which is insertable into the lumen (2) when the mandrel sleeve (16) is in a removed condition.

5. A catheter according to claim 4, comprising a distal stop (15) for the piercing motion of the removable mandrel sleeve (16) being disposed in the lumen (2) between the sealing unit (13) and the sluice gate (11), wherein the distal stop (15) and the proximal stop (19) are formed by graduations in diameter in the form of annular shoulders, an inside diameter (D1) of the lumen (2) at the distal stop (15) being less than an inside diameter (D2) at the proximal stop (19).

6. A catheter according to claim 5, wherein the counterpart on the mandrel (20) is a ball (21), a diameter (A2) of which is greater than the inside diameter (D2) of the proximal stop (19).

7. A catheter according to claim 4, comprising catheter electrodes (5), wherein the mandrel (20) is electrically insulated towards electric connecting lines (4) for the catheter electrodes (5).

* * * * *